(12) United States Patent
Baker et al.

(10) Patent No.: US 7,021,485 B1
(45) Date of Patent: Apr. 4, 2006

(54) CONTAINER FOR STERILIZATION

(75) Inventors: Terry L. Baker, Boggstown, IN (US);
Bernie B. Berry, III, Indianapolis, IN (US)

(73) Assignee: Carr Metal Products, Inc., Indianapolis, IN (US)

( * ) Notice: Subject to any disclaimer, the term of this patent is extended or adjusted under 35 U.S.C. 154(b) by 58 days.

(21) Appl. No.: 10/218,345

(22) Filed: Aug. 14, 2002

Related U.S. Application Data

(60) Continuation-in-part of application No. 09/634,072, filed on Aug. 8, 2000, now Pat. No. 6,896,149, which is a division of application No. 09/020,889, filed on Feb. 9, 1998, now Pat. No. 6,138,850.

(60) Provisional application No. 60/371,188, filed on Apr. 9, 2002.

(51) Int. Cl.
*B65D 45/16* (2006.01)
(52) U.S. Cl. .................................................. 220/326
(58) Field of Classification Search ................ 220/324, 220/326, 4.33
See application file for complete search history.

(56) References Cited

U.S. PATENT DOCUMENTS

| | | | |
|---|---|---|---|
| 3,360,152 A * | 12/1967 | Leers | 220/4.24 |
| 3,528,583 A | 9/1970 | Taylor | |
| 3,854,582 A | 12/1974 | Martinelli | |
| 3,966,285 A * | 6/1976 | Porch et al. | 312/265.4 |
| 3,987,924 A | 10/1976 | Uitz | |
| 4,186,841 A | 2/1980 | Buckley et al. | |
| 4,366,905 A | 1/1983 | Forshee | |
| 4,643,303 A | 2/1987 | Arp et al. | |
| 4,762,688 A | 8/1988 | Berry, Jr. | |
| 4,798,292 A | 1/1989 | Hauze | |
| 5,084,251 A | 1/1992 | Thomas | |
| 5,215,726 A | 6/1993 | Kudla et al. | |
| 5,284,632 A | 2/1994 | Kudla et al. | |
| 5,310,049 A | 5/1994 | Bigelow et al. | |
| 5,312,011 A | 5/1994 | Fischer | |
| 5,346,677 A | 9/1994 | Risk | |
| 5,372,787 A | 12/1994 | Ritter | |
| 5,415,846 A | 5/1995 | Berry, Jr. | |
| 5,424,048 A | 6/1995 | Riley | |
| 5,433,929 A | 7/1995 | Riihimaki et al. | |
| 5,441,709 A | 8/1995 | Berry, Jr. | |
| 5,451,379 A | 9/1995 | Bowlin, Jr. | |
| 5,460,288 A * | 10/1995 | Balzeau | 220/326 |
| 5,474,196 A | 12/1995 | Fausel et al. | |
| 5,518,115 A | 5/1996 | Latulippe | |
| 5,524,755 A | 6/1996 | Deeds | |
| 5,540,901 A | 7/1996 | Riley | |
| 5,560,508 A | 10/1996 | Hsu | |
| 5,593,058 A | 1/1997 | Spencer et al. | |
| 5,641,065 A | 6/1997 | Owens et al. | |

(Continued)

FOREIGN PATENT DOCUMENTS

GB  2 298 578 A  9/1996

*Primary Examiner*—Stephen Castellano
(74) *Attorney, Agent, or Firm*—Woodard, Emhardt, Moriarty, McNett & Henry LLP

(57) ABSTRACT

A modular container for sterilization of medical devices. In various embodiments the container includes a slidable button for releasing the lid, the button being contained within a pocket. Other embodiments include a lid and container bottom arranged so that a pair of stacked containers have a gap between the lid and bottom to facilitate drying of the container contents. Yet other embodiments include arrangement of the container sidewalls to fit within the sides of the lid.

1 Claim, 18 Drawing Sheets

U.S. PATENT DOCUMENTS

| | | |
|---|---|---|
| 5,678,717 A | 10/1997 | Hsu |
| 5,706,968 A * | 1/1998 | Riley .................. 220/326 |
| 5,765,707 A | 6/1998 | Kenevan |
| 5,843,387 A | 12/1998 | Dane et al. |
| 5,851,484 A | 12/1998 | Forno et al. |
| 5,913,422 A | 6/1999 | Cote et al. |
| 5,918,740 A | 7/1999 | Berry, Jr. |
| 6,099,812 A | 8/2000 | Allen et al. |
| 6,116,452 A | 9/2000 | Hamel et al. |
| 6,138,850 A | 10/2000 | Berry, III |
| 6,193,932 B1 | 2/2001 | Wu et al. |
| 6,210,638 B1 | 4/2001 | Grieco et al. |
| 6,217,835 B1 | 4/2001 | Riley et al. |
| 6,237,770 B1 | 5/2001 | Bowsman |
| 6,244,447 B1 | 6/2001 | Frieze et al. |
| 6,248,293 B1 | 6/2001 | Davis et al. |
| 6,264,902 B1 | 7/2001 | Howlett |
| 6,319,481 B1 | 11/2001 | Banks |
| 6,331,280 B1 | 12/2001 | Wood |
| 6,350,418 B1 | 2/2002 | Venderpool et al. |
| 6,365,115 B1 | 4/2002 | Wood |

* cited by examiner

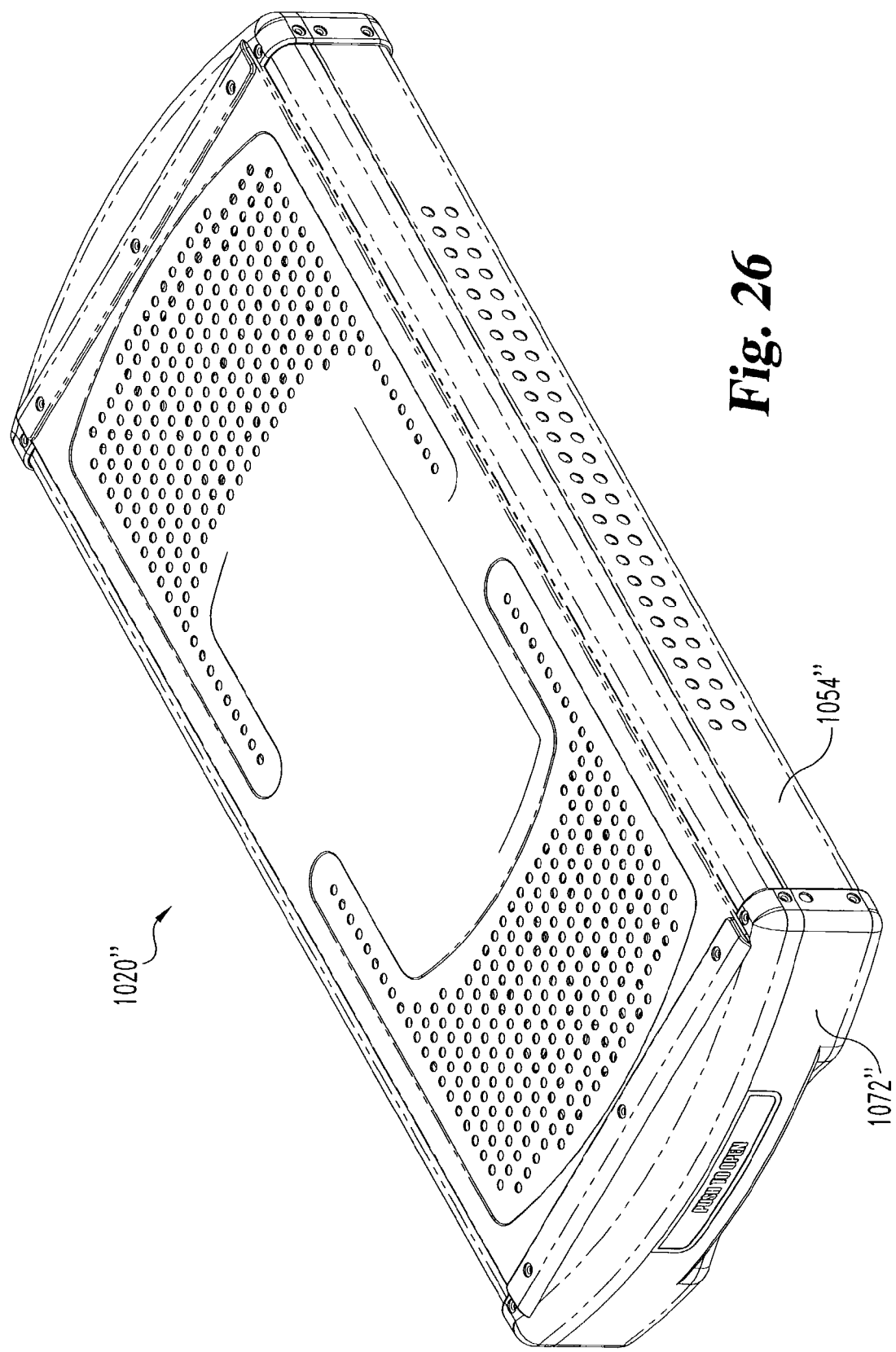

CONTAINER FOR STERILIZATION

This application is a continuation-in-part application of and claims priority to divisional application Ser. No. 09/634,072 filed Aug. 8, 2000 now U.S. Pat. No. 6,896,149 which is divisional application of and claims priority to U.S. patent application Ser. No. 09/020,889, filed Feb. 9, 1998 now U.S. Pat. No. 6,138,850. This application also claims priority to provisional patent application Ser. No. 60/371,188, filed Apr. 9, 2002. All of these patent applications are incorporated herein by reference.

BACKGROUND OF THE INVENTION

The present invention relates generally to containers useful for sterilization of medical devices. However, certain applications of the present invention may be outside of this field.

The use of a container for the sterilization and storage of medical devices is well known. The container is provided with a particular selection of devices for a particular medical procedure. The devices are placed within a container and the container is then subjected to the heat and sterilant (water and/or chemicals) necessary to sterilize the devices. Subsequent to sterilization, the container may be wrapped within a sterile covering and stored until required.

Various designs have been offered for sterilization containers. Some of these designs can be found in the following U.S. patents:

| U.S. Pat. No. | Inventor | Issue Date |
| --- | --- | --- |
| 4,798,292 | Hauze | Jan. 17, 1989 |
| 4,643,303 | Arp et al. | Feb. 17, 1987 |
| 5,284,632 | Kudla et al. | Feb. 8, 1994 |
| 5,215,726 | Kudla et al. | Jun. 1, 1993 |
| 5,451,379 | Bowlen, Jr. | Sep. 19, 1995 |
| 5,524,755 | Deeds | Jun. 11, 1996 |
| 5,084,251 | Thomas | Jan. 28, 1992 |
| 5,433,929 | Riihimaki et al. | Jul. 18, 1995 |
| 5,346,677 | Risk | Sep. 13, 1994 |
| 5,518,115 | Latulippe | May 21, 1996 |
| 5,540,901 | Riley | Jul. 30, 1996 |
| 5,424,048 | Riley | Jun. 13, 1995 |

These designs generally depict containers comprising a lower tray and an upper tray or lid. The lower and upper trays are generally of a fixed, unitary construction. The lower tray and the upper tray or lid are generally of a particular size and shape which cannot be altered without damaging or destroying the trays. Some of these designs have an internal volume satisfactory for the quantity of devices necessary for a particular medical procedure, but insufficient volume for a larger number of devices required by a different medical procedure. Likewise, the containers resulting from some of these designs may be too large for a particular medical procedure, and thus be inefficient in terms of space and costs.

There is a continuing need for improvements in the field of sterilization containers and the present invention provides a novel and unobvious apparatus for an improved sterilization container.

SUMMARY OF THE INVENTION

One embodiment of the present invention provides a container for sterilization of medical devices. The container includes a base defining a plurality of through holes, four walls, and a bottom. There is also a button actuateable between an extended position and a depressed position; and a lid releaseably coupled to the base and releasable therefrom by actuation of the button. The button is slidable within a pocket formed by the lid and the base.

Another embodiment of the present invention relates to a container for sterilization of devices which includes an underside having a central portion and a bottom spacing feature, and a topside having a central portion and a top spacing feature adapted and configured to nest with the bottom spacing feature. During stacking of a first container on top of a second container the bottom spacing feature of the first container and the top spacing feature of the second container nest together, the bottom spacing feature and the top spacing feature being adapted and configured to establish a gap extending between the central portion of the underside and the central portion of the topside, the gap permitting flow of gas therebetween.

Yet another embodiment of the present invention concerns a container for sterilization of medical devices which includes a base including first and second endwalls and a base midsection having a bottom with integral or separable third and fourth opposing sidewalls, each third and fourth sidewall including a first edge projecting from a lengthwise ridge. The container also includes a lid including a lid midsection with a top and an integral or separable pair of opposing sides, each said side including a second edge. The lid fits on the base with the edge of each side being supported by a ridge of a corresponding sidewall and each second edge being displaced from the corresponding first edge.

Another embodiment of the present invention concerns a container for sterilization of devices which includes a base having a button sidably retained thereto. The button has a first position and a second position, and the base includes a first latching member. There is also a lid releaseably coupleable to said base and including a second latching member which couples to the first latching member to retain the lid on said base. Sliding of the button to the second position uncouples the second latching member from the first latching member.

It is an object of the present invention to provide an improved container for serialization of medical devices.

These and other objects and advantages of the present invention will be apparent from the description of the preferred embodiment, the drawings, and the claims that follow.

BRIEF DESCRIPTION OF THE DRAWINGS

FIG. 6 is a right side perspective view of the apparatus of FIG. 4 with a portion of the apparatus pushed in.

FIG. 26 is a top, front, and left side perspective view of an apparatus according to another embodiment of the present invention.

DESCRIPTION OF THE PREFERRED EMBODIMENT

Figure 1A:
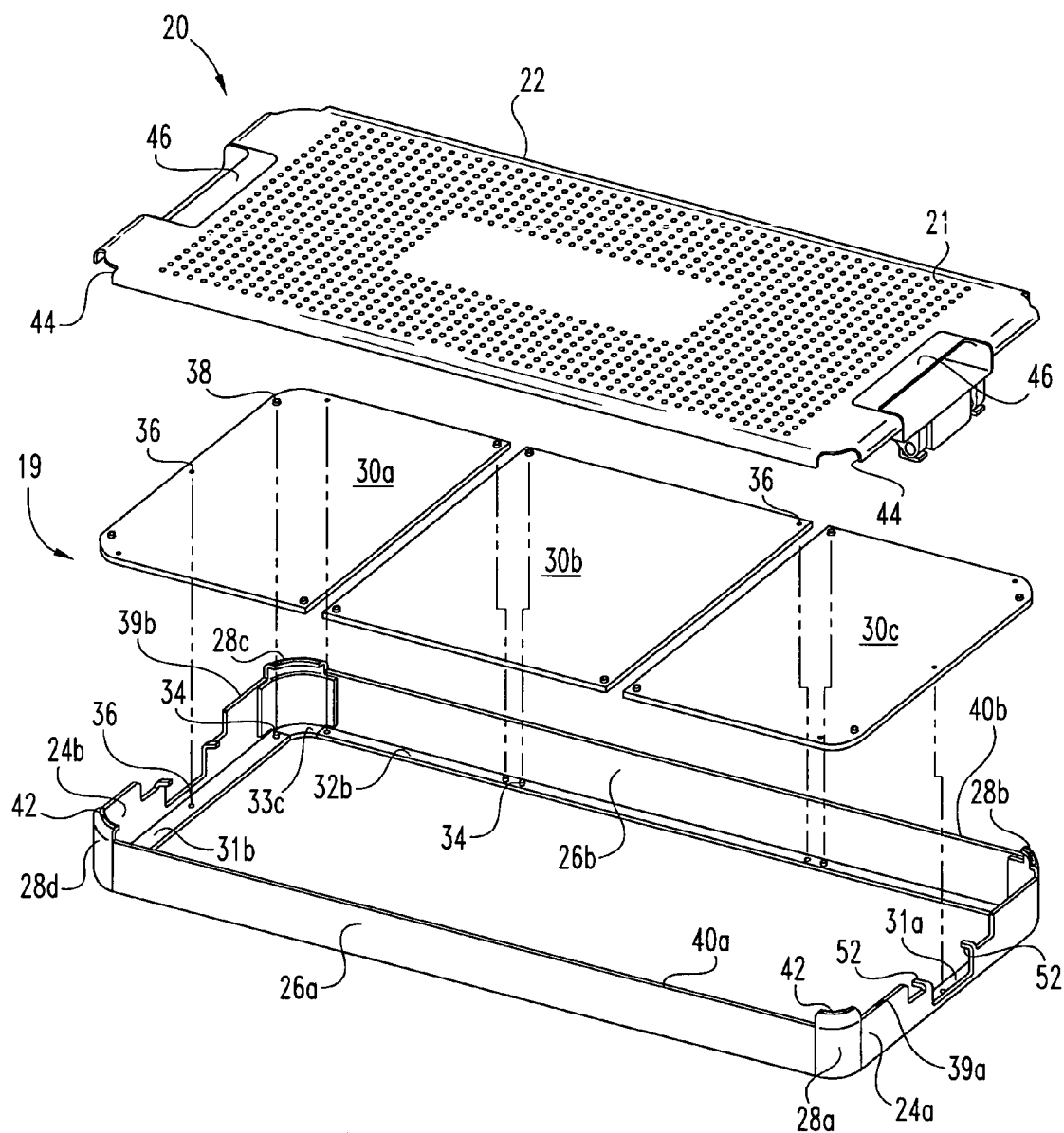
FIG. 1A is a top, front, and right side exploded perspective view of an apparatus according to one embodiment of the present invention.

For the purposes of promoting an understanding of the principles of the invention, reference will now be made to the embodiment illustrated in the drawings and specific language will be sued to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

FIG. 1A is a top, front, and right side exploded perspective view of a sterilization container 20 useful for sterilization of medical instruments and devices according to one embodiment of the present invention. Container 20 includes a tray assembly 19 and a removable lid 22. The tray assembly includes opposing separable sides 24a and 24b, opposing separable sides 26a and 26b, corner pieces 28a, 28b, 28c, and 28d, and bottom pieces 30a, 30b, and 30c. Removable lid 22 includes a plurality of passage holes 21 defined therein for passage of sterilant fluid into and out of the interior of container 20. Lid 22 is releaseably coupled to opposing separable sides 24a and 24b by a latching mechanism to be described later (see FIGS. 3–9). Separable side 24a is coupled at one end to corner piece 28a and at the other end to corner piece 28b. Separable side 24b is coupled at one end to corner piece 28c and at the other end to corner piece 28d. Separable side 26a is coupled to corner pieces 28a and 28d, and separable side 26b is coupled to corner pieces 28b and 28c. Separable sides 26a and 26b are of a predetermined, modular length.

A bottom panel 30 comprising bottom pieces 30a, 30b, and 30c is in contact with and preferably supported by substantially flat ledges that extend in a generally perpendicular manner from the vertical walls of separable sides 24a, 24b, 26a, and 26b. Separable sides 24a and 24b include ledges 31a and 31b, respectively, for supporting bottom pieces 30c and 30a, respectively. Separable sides 26a and 26b include ledges 32a and 32b, respectively, for supporting bottom pieces 30a, 30b, and 30c. Additional support of bottom panel 30 is preferably provided by substantially flat ledges that extend from the corner pieces. Ledges 33a and 33b of corner pieces 28a and 28b, respectively, support bottom piece 30c. Ledges 33c and 33d of corner pieces 28c and 38d, respectively, support bottom piece 30a. In some embodiments of the present invention bottom panel 30 defines a plurality of attachment holes (not shown) to which fixtures may be attached which are useful for clamping medical devices thereto.

Ledges 31a, 31b, 32a, and 32b incorporate a combination of pins 34 and fastener holes 36 that align with locating holes 38 and fastener holes 36, respectively, on bottom panel 30. Fasteners (not shown) fasten bottom piece 30a to ledges 32a, 32b, and 31b. Bottom piece 30c is similarly fastened to ledges 32a, 32b, and 31a. Bottom piece 30b is fastened to ledges 32a and 32b. Pins 34 protrude through locating holes 38 and generally align bottom panel 30 relative to sides 24a, 24b, 26a, and 26b. Bottom panel 30 preferably includes a short cylinder protruding above the upper surface of bottom panel 30 and around hole 38 so as to provide additional bearing area for pin 34. However, the present invention also contemplates a locating hole 38 defined only within bottom panel 30. Also, although it is preferable to include pins 34 and fastener holes 36 within ledges 31a, 31b, 32a, and 32b, the present invention also contemplates pins 34 or fastener holes 36 as part of ledges 33a, 33b, 33c, and 33d of corner pieces 28a, 28b, 28c, and 28d, respectively. Bottom pieces 30a, 30b, and 30c are repeatedly separable from sides 24a, 24b, 26a, and 26b, and/or from corners 28a, 28b, 28c, and 28d, by removal of the fasteners through holes 36.

Figure 1B:
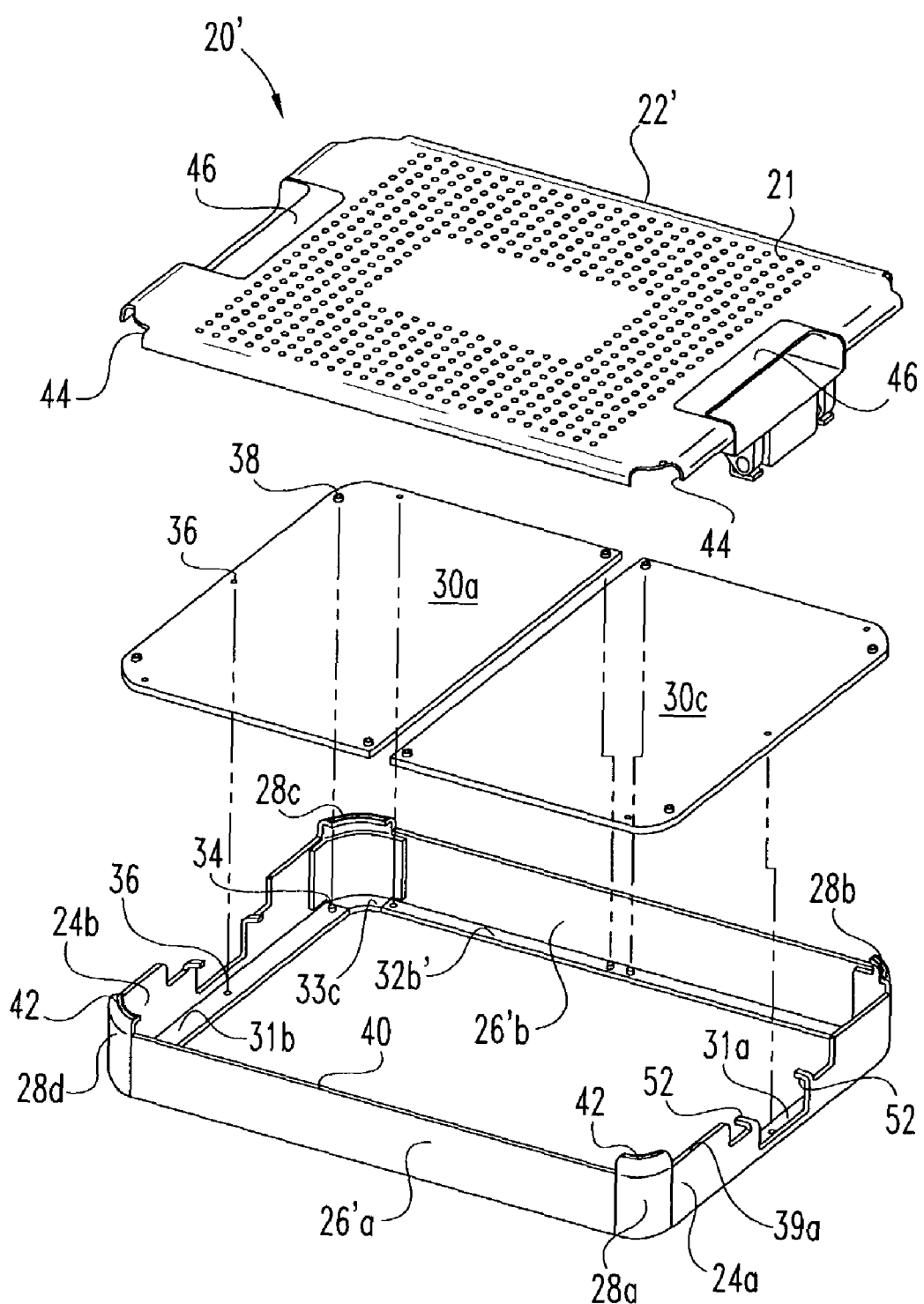
FIG. 1B is a top, front, and right side exploded perspective view of an apparatus according to another embodiment of the present invention.

FIG. 1A shows one embodiment of the present invention in which three bottom pieces 30a, 30b, and 30c provide a bottom panel 30 of a predetermined length useful with the predetermined lengths of opposing sides 26a and 26b. However, the present invention contemplates modularity of the length of container 20, and thus modularity of the internal volume of container 20. A container 20' is shown in FIG. 1B. Container 20' incorporates a lid 22' of a shorter length than lid 22. Container 20' also includes opposing sides 26a' and 26b' of a shorter length than opposing sides 26a and 26b. Bottom panel 30' comprises bottom pieces 30a and 30c, with bottom piece 30b being omitted. Thus, container 20 with a first, larger internal volume may be converted into a container 20' with a second, smaller internal volume by substitution of separable side 26a' for 26a, substitution of separable side 26b' for separable side 26b, omission of bottom piece 30b, and substitution of lid 22'. Container 20 my also be converted into a container (not shown) with an internal volume larger than the internal volume of container 20. One improvement offered by the present invention is that a healthcare provider such as a hospital can reduce its equipment cost by rebuilding sterilization containers made in accordance with the present invention into different sizes, both larger and smaller than apparatus 20, and thus avoid the cost of purchasing new containers.

Although apparatus 20 and 20' have been described having multi-piece bottom panels 30 and 30', respectively, the present invention also contemplates a single piece bottom panel 30 and a single piece bottom panel 30' of different lengths. Further, although apparatus 20 and 20' have been described incorporating a plurality of corner pieces separable from the sides of the container, the present invention also contemplates those embodiments in which corner pieces are integral with sides otherwise similar to sides 24a and 24b. In these embodiments the corner pieces are not separable from the sides, but modularity of the present invention is maintained by the separability of opposing sides 26a and 26b.

Corner pieces 28a–d include a first alignment feature 42 that is preferably spaced above the upper surfaces of adjacent separable sides. Lid 22 includes a second alignment feature 44 which is generally complementary in shape to first alignment feature 42. Coupling of lid 22 to sides 24a and 24b results in coupling of first alignment feature 42 with second alignment feature 44. Separable sides 24a and 24b incorporate upper surfaces 39a and 39b, respectively, and separable sides 26a and 26b incorporate upper surfaces 40a and 40b, respectively. Although one embodiment of the present invention includes a first alignment feature 42 spaced above the upper surfaces of the separable sides, the present invention also contemplates those embodiments in which first alignment feature 42 is recessed below upper surfaces 39a, and 39b, and 40a and 40b, and second alignment feature 44 includes a protrusion to fit within the recess. Also, although upper surfaces 39a, 39b, 40a, and 40b are generally at the same elevation above bottom panel 30, the present invention also contemplates upper surfaces 39a, 39b, 40a, and 40b that are at different elevations.

Figure 2:
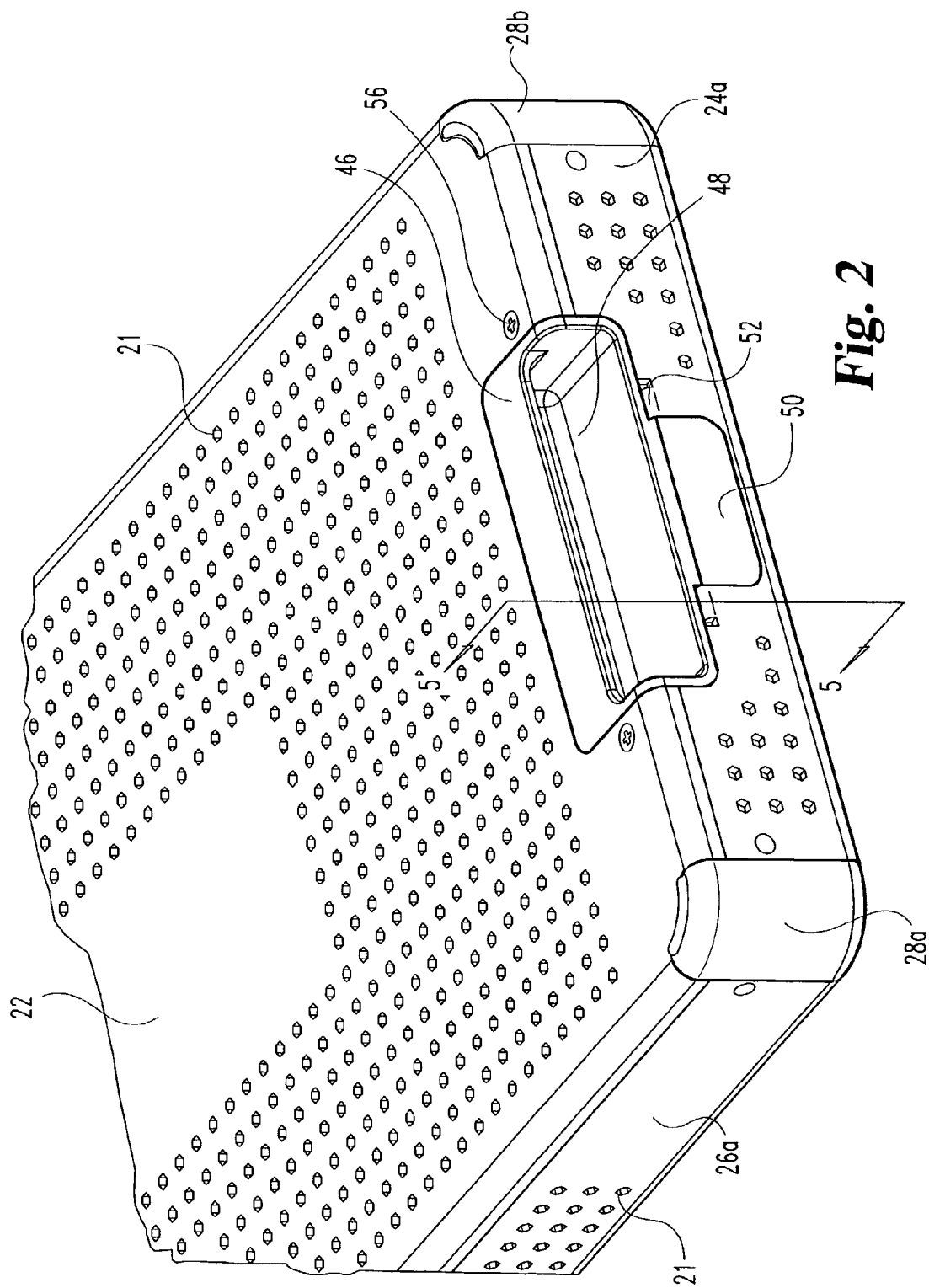
FIG. 2 is a partial perspective view of a portion of the apparatus of FIG. 1A.

Lid 22 includes a pair of handles 46 on opposing ends of lid 22 as best seen in FIGS. 1A, 1B, and 2. Handle 46 includes within it a pocket 48 for carrying container 20. Pocket 48 has a shape suitable for insertion of human fingers. Lid 22 also includes a button 50 coupled to lid 22 and moveable relative to lid 22. Handle 46 is attached to lid 22 by a pair of ears 54 best seen in FIG. 3 and FIG. 4. A pair of flush mounted fasteners 56 attach handle 46 to lid 22 through ears 54.

Figure 3:
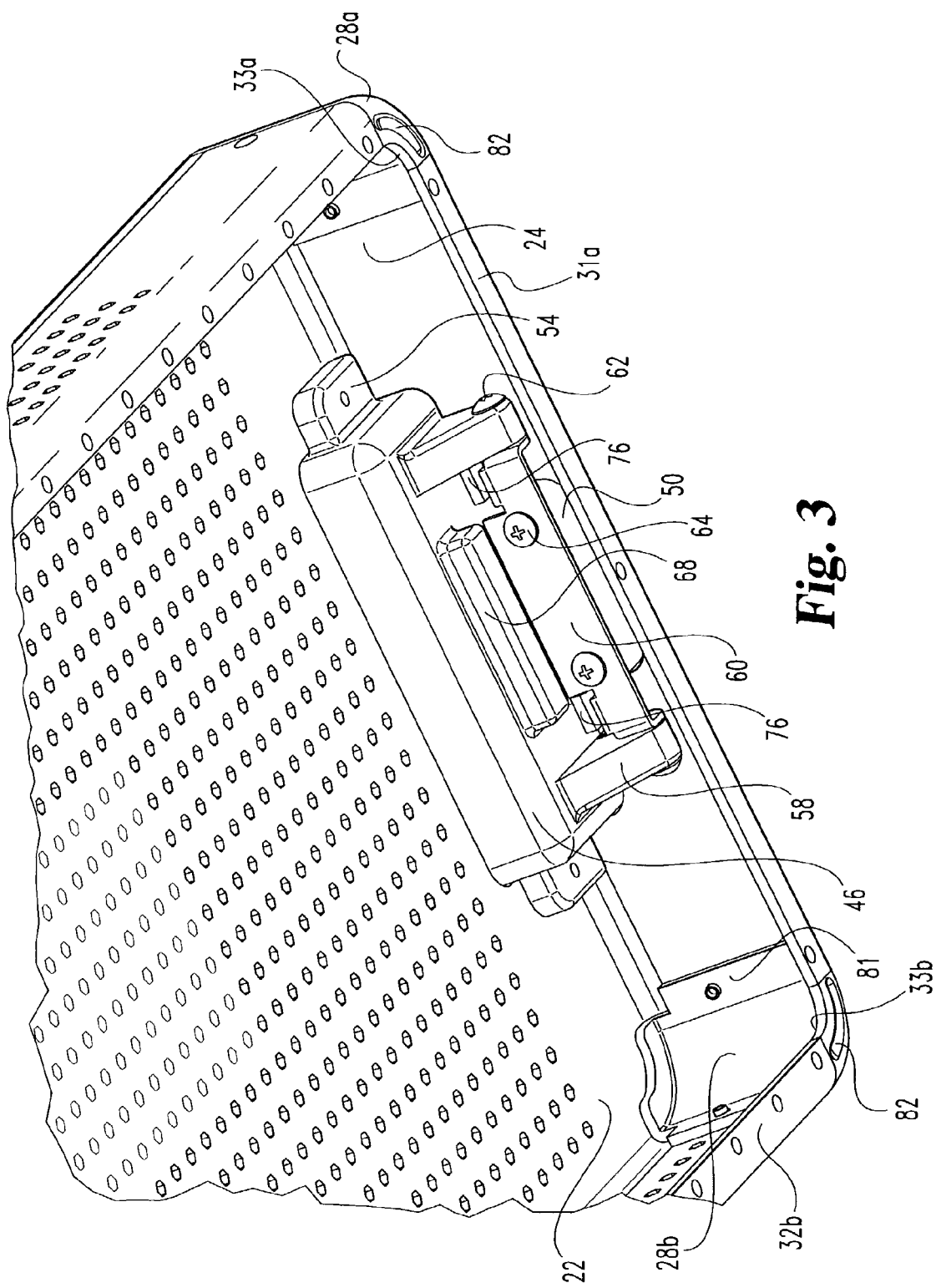
FIG. 3 is a partial perspective view of a portion of the apparatus of FIG. 1A with a bottom piece removed.
Figure 4:
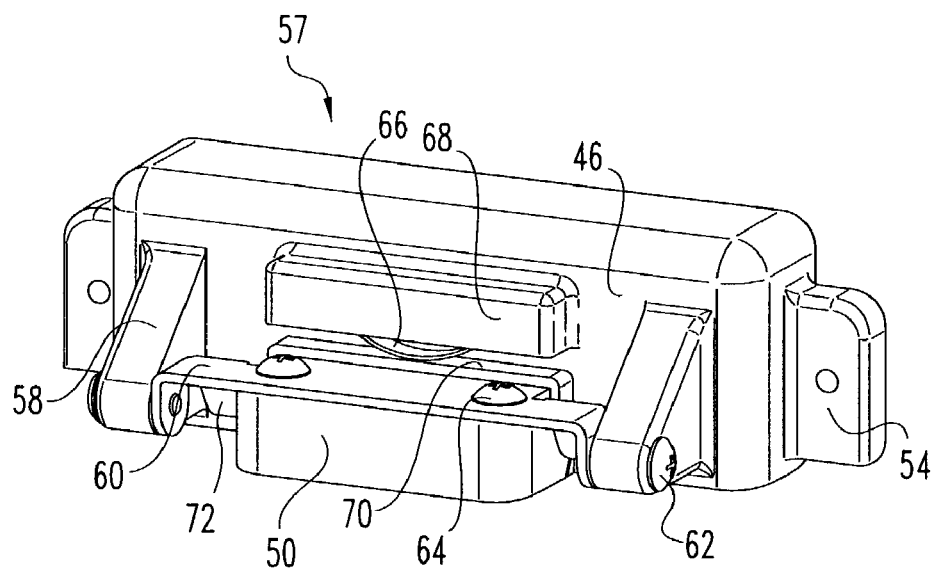
FIG. 4 is a bottom perspective view of a handle assembly comprising a portion of the present invention.

Handle 46 and button 50 are substantially flush with the exterior surface of container 20. The exterior surface of container 20 is also generally smooth. By being generally smooth and not having abrupt protrusions beyond its exterior surfaces, container 20 is especially suitable for being wrapped in a protective covering after sterilization with little danger of the protective covering being ripped, abraded, broken, or damaged by the exterior surface of container 20. FIGS. 2 and 3 also show a plurality of holes 21 for passage of sterilant defined within sides 24 and 26. In some embodiments of the present invention a plurality of holes 21 for passage of sterilant are defined within bottom panel 30.

Sides 24a and 24b each include a pair of stationary tabs 52 which are generally flush with the exterior surface of sides 24a and 24b, and which project inwardly toward the interior of container 20, as best seen in FIG. 1. Stationary tabs 52, along with other elements of the latching mechanism of container 20 provides a means for releaseably coupling lid 22 to sides 24a and 24b. The latching mechanism of apparatus 20 is best understood by referring to FIGS. 3, 4, 5, and 6. Extending generally downward from the underside of handle 46 is a pair of supports 58. A latchplate 60 is pivotally connected to supports 58 by a pair of pivoting fasteners 62 operating through pivot hole 63a of support 58 and hole 63b of latchplate 60 (see FIGS. 7 and 9). Button 50 is coupled to latchplate 60 by a pair of fasteners 64, and is moveable with latchplate 60. A spring 66 located within a spring retainer 68 presses against back surface 70 of button 50 and thus urges button 50 and latchplate 60 to pivot in a direction whereby upper exterior surface 71 of button 50 is urged outward.

Figure 5:
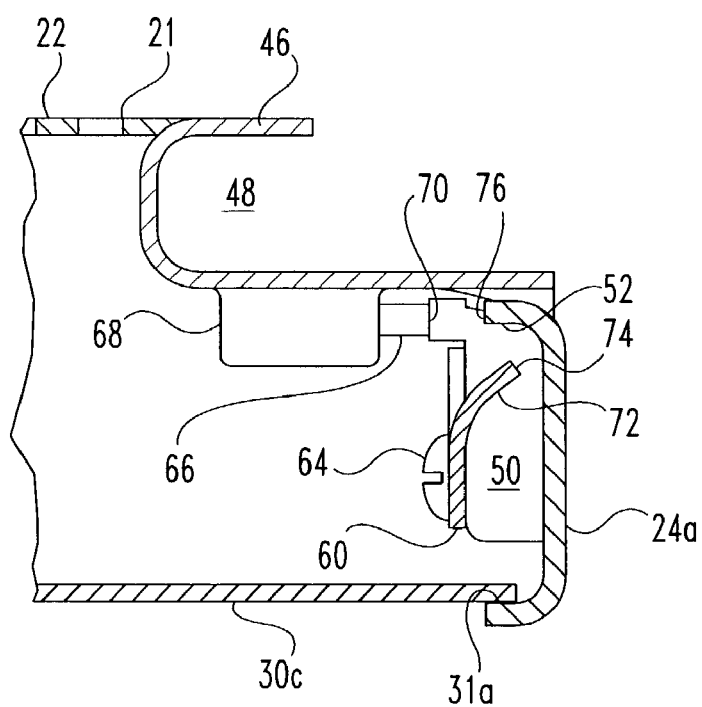
FIG. 5 is a partial front elevational view in full section of the apparatus of FIG. 2 as taken along line 5—5 of FIG. 2.
Figure 6:
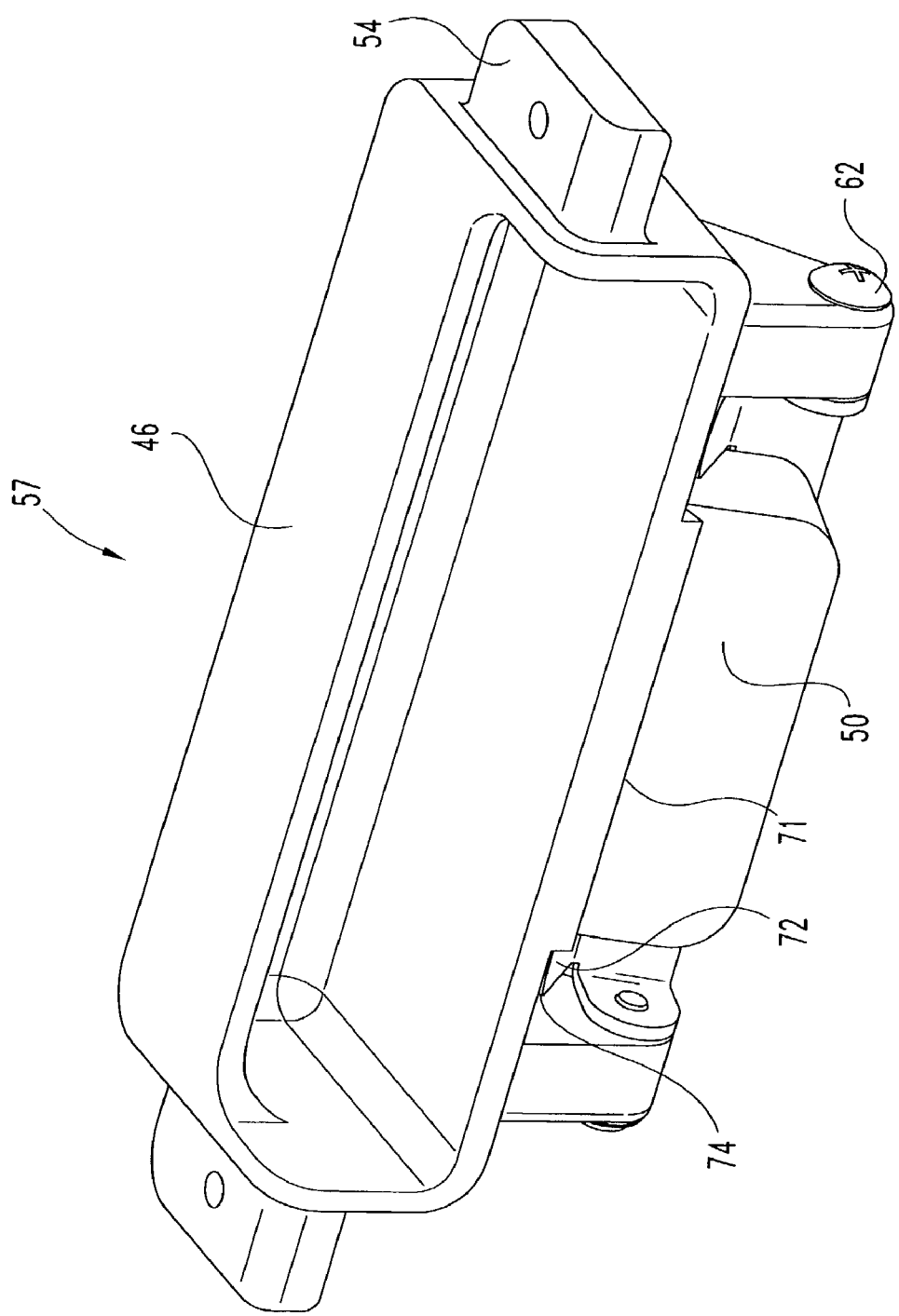

Latchplate 60 incorporates a pair of tabs 72 moveable with latchplate 60 and button 50. These moveable tabs 72 extend upward and outward at an angle as best seen in FIG. 5. Moveable tab 72 has an edge 74 which is proximate to the underside of stationary tab 52 when lid 22 is releaseably coupled to sides 24a and 24b. Thus, when container 20 is picked up by handle 46, edge 74 of moveable tab 72 engages the underside of tab 52 and does not permit lid 22 to uncouple from sides 24a and 24b. To release lid 22 from its coupling with sides 24a and 24b, button 50 is pushed in along upper surface 71 of button 50 (see FIG. 6). Button 50, latchplate 60, and moveable tabs 72 will thus rotate into the interior of container 20. As moveable tabs 72 pivot, edge 74 moves past edge 76 of stationary tab 52. Once edge 74 has moved clear of edge 76, lid 22 may be lifted vertically and uncoupled from sides 24a and 24b. As upper surface 71 of button 50 is pushed inward toward the interior of container 20, semi-circular guide 75 of handle assembly 57 provides a guide for guided surface 77 of button 50 (see FIG. 8).

Although button 50 and moveable tabs 72 have been shown and described as moving in a pivotal manner, the present invention also contemplates a button and moveable tabs that move linearly within container 20 when pushed. This linear movement button and linear movement tabs would be guided along support rails coupled to supports extending from the handle. The means for releaseably coupling lid 22 to container 20 includes a stationary tab 52, a moveable tab 72, and a button 50 for moving moveable tab 72, the movement being rotational, linear, or a combination of the two.

Figure 7:
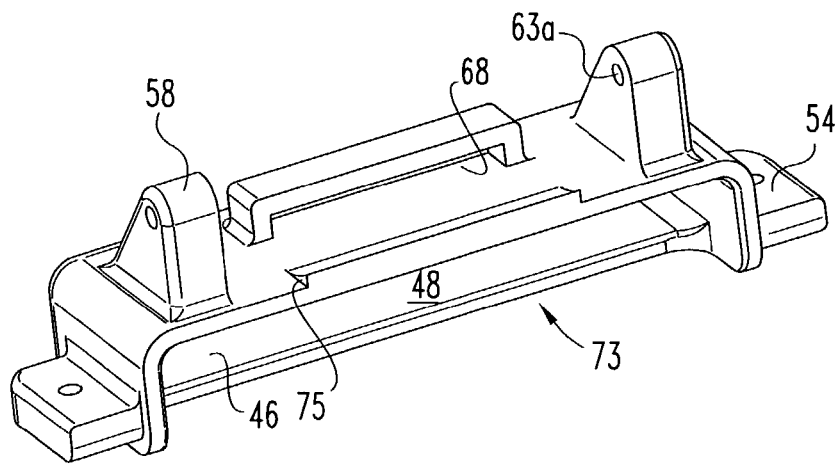
FIG. 7 is a perspective view of a handle molding comprising a portion of the present invention.
Figure 8:
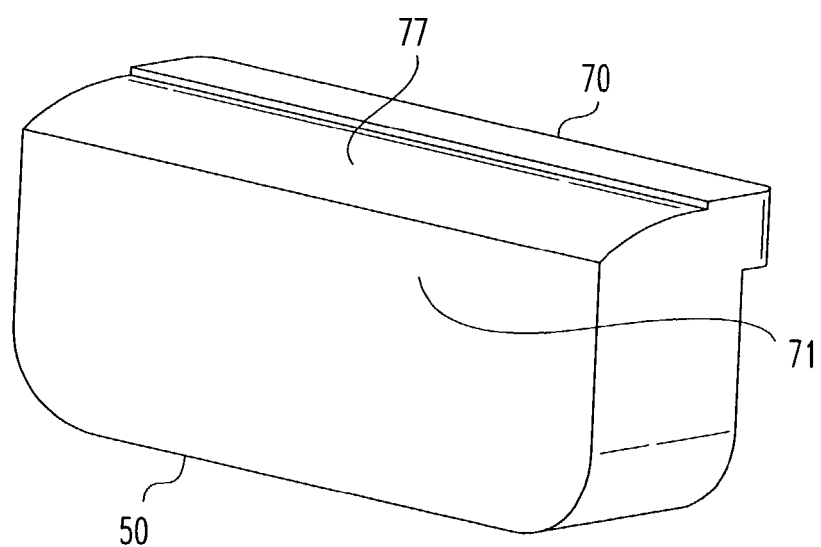
FIG. 8 is a perspective view of a button comprising a portion of the present invention.

A handle molding 73 comprising a portion of the present invention is shown in FIG. 7. Handle molding 73 shows a preferable combination of handle 46, ears 54, supports 58, spring retainer 68, and semi-circular guide 75, all molded within a single part. However, the present invention also contemplates those embodiments in which the aforementioned pieces may be separately fabricated and attached together as an assembly.

Figure 9:
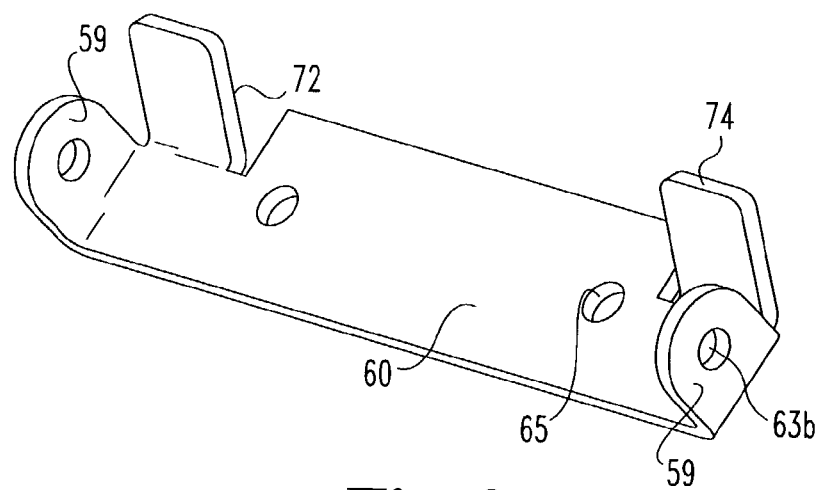
FIG. 9 is a perspective view of a latchplate comprising a portion of the present invention.

Latchplate 60 is shown apart from button 50 in FIG. 9. In a preferred embodiment, latchplate 60 is fabricated from a metal such as a corrosion resistant stainless steel. However, the present invention also contemplates those embodiments in which moveable tabs 72 are molded integrally onto button 50.

Figure 10:
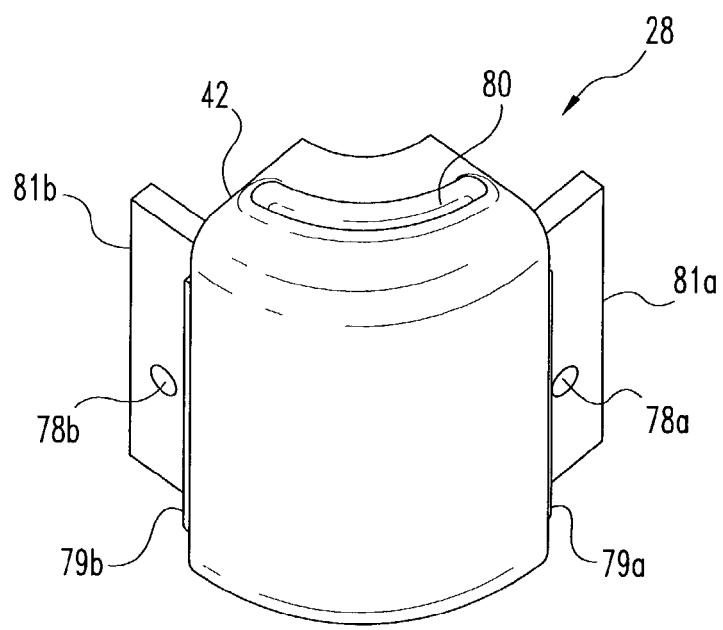
FIG. 10 is a perspective view of a corner piece comprising a portion of the present invention.

FIG. 10 is a top perspective view of a corner piece 28 comprising a portion of the present invention, and shown previously as corner pieces 28a, 28b, 28c, and 28d. Corner piece 28 has a generally smooth, rounded exterior surface and encompasses about 90 degrees of circular arc. Preferably projecting from either end 79a and 79b of corner piece 28 is an attachment ear 81a and 81b, respectively. A side 24a, 24b, 26a, or 26b may be attached to a corner piece 28 by placing the edge of the side in contact with surface 72a, and the interior surface of the side in contact with attachment 81a. A fastener fastens a side 26a, 26b, 24a, or 24b to corner piece 28 through fastener hole 78a. By removing the fastener from fastener hole 78a, corner pieces 28 are separable from container 20. For simplicity of manufacturing and assembly and reduction in cost, corner pieces 28a, 28b, 28c, and 28d, are preferably identical. The present invention also contemplates a corner piece in which the attachment ears are integrated into the separable sides, and the corner piece includes a pocket shaped to slidably accept the attachment ear.

Corner 28 includes a smooth, recessed first locating feature 80 on the top surface of corner 28. This first locating feature 80 is capable of being coupled to a second raised locating feature 82 on the bottom of corner piece 28 (refer to FIG. 3). Locating features 80 and 82 are useful for stacking of one container 20 on top of another container 20. Raised locating feature 82 can be coupled within recessed locating feature 80 and thus stabilize the position of the top container 20 relative to the position of the bottom container 20. It is preferable that locating features 80 and 82 be complementary in shape, such that the shape of feature 82 fits within the recessed shape of feature 80. It is also preferable that locating features 80 and 82 be incorporated on each corner piece 28. However, the present invention also contemplates those embodiments in which locating features 80 and 82 are present on only two of the corner pieces. Further, the present invention also contemplates a locating feature 82 that couples to locating feature 80, but is not necessarily complementary in shape thereto.

Figure 11:
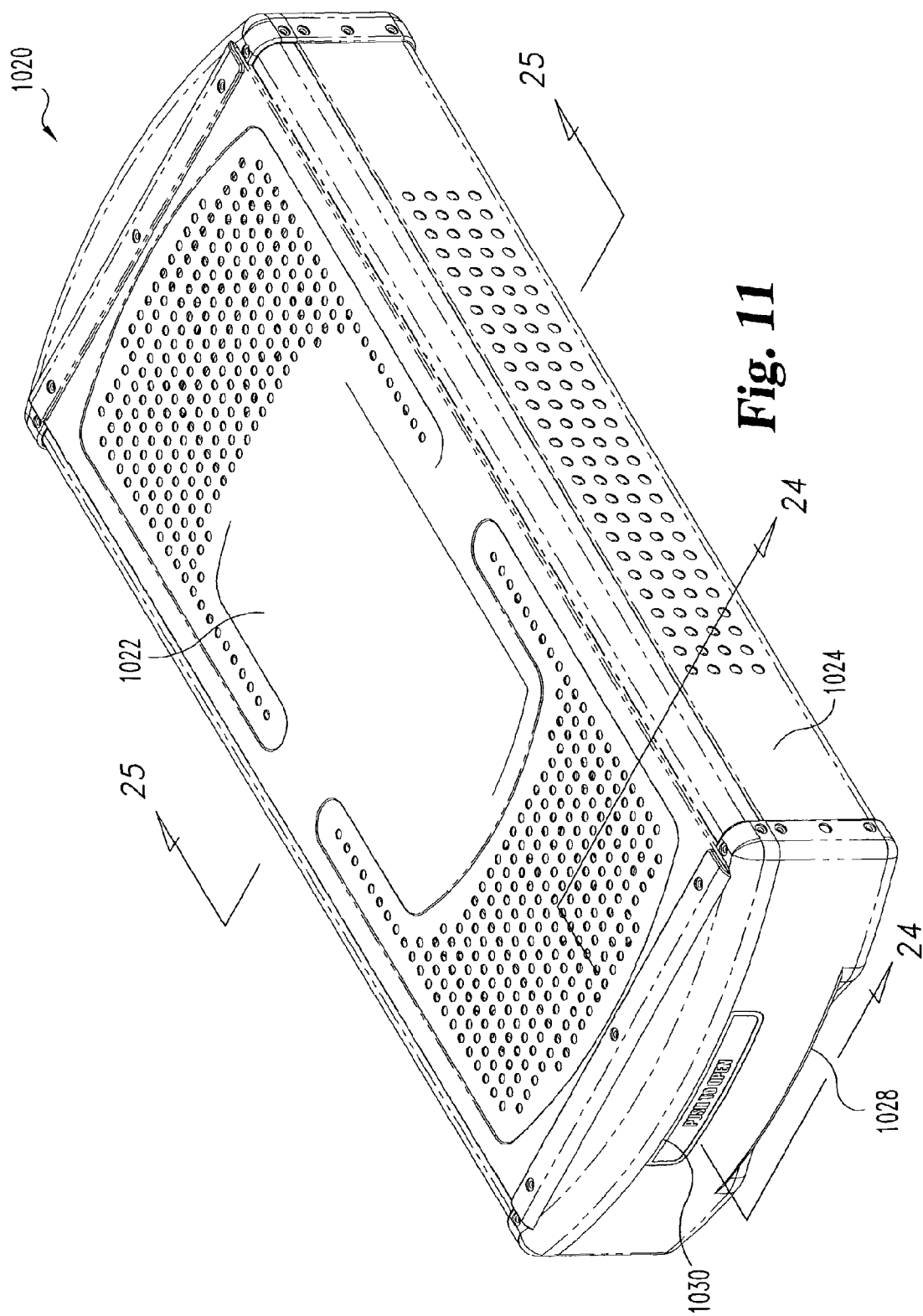
FIG. 11 is a top, front, and left side perspective view of an apparatus according to another embodiment of the present invention.

FIGS. 11–26 depict various views of sterilization containers according to other embodiments of the present invention. FIG. 11 shows a perspective view of a sterilization container 1020 according to another embodiment of the present invention. Container 1020 includes a lid 1022 which fits on top of a base 1024. Container 1020 includes a pair of handles 1028 which are recessed into opposing endwalls of the container. Handles 1028 are used for lifting of the container. Preferably located above each handle 1028 is a button 1030 which releaseably couples and uncouples lid 1022 to base 1024.

Figure 12:
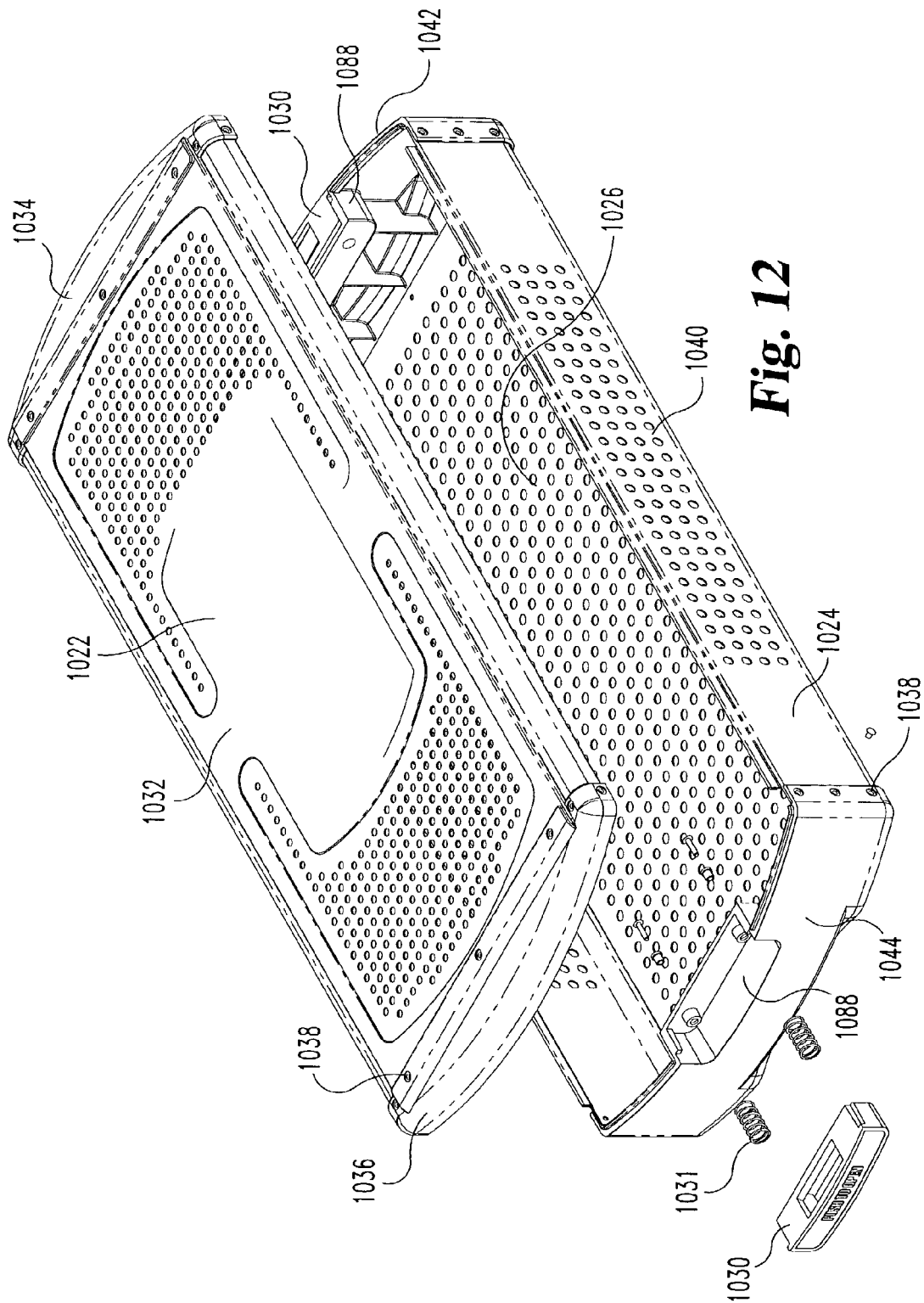
FIG. 12 is a partially exploded view of the apparatus of FIG. 11.

FIG. 12 is a partially exploded view of the container of FIG. 11. Lid 1022 is shown raised above the corresponding fitment edges of base section 1024. Lid 1022 includes a lid midsection 1032 and a pair of endpieces 1034 and 1036, each endpiece being fastened by a plurality of fasteners 1038 to opposing sides of midsection 1032. Base 1024 includes a base midsection 1040 with a pair of opposing endwalls 1042 and 1045 fastened by a plurality of fasteners 1038 to opposing ends of base midsection 1040. Base section 1040 comprises a bottom and four opposing sides that define an interior 1026 in which medical instruments or other devices are retained during sterilization and storage. When lid 1022 is placed on based 1024, each endpiece 1034 and 1036 is supported by a corresponding endwall 1042 and 1044, respectively. Further, the other two opposing sides of lid midsection 1032 are supported upon opposing sides of base midsection 1040. FIG. 12 also shows a button 1030 in exploded view and removed from a corresponding pocket 1088. Attachment hardware for button 1030, including a pair of biasing springs 1031, a pair of collars, and a pair of fasteners are also shown in exploded view.

Figure 13:
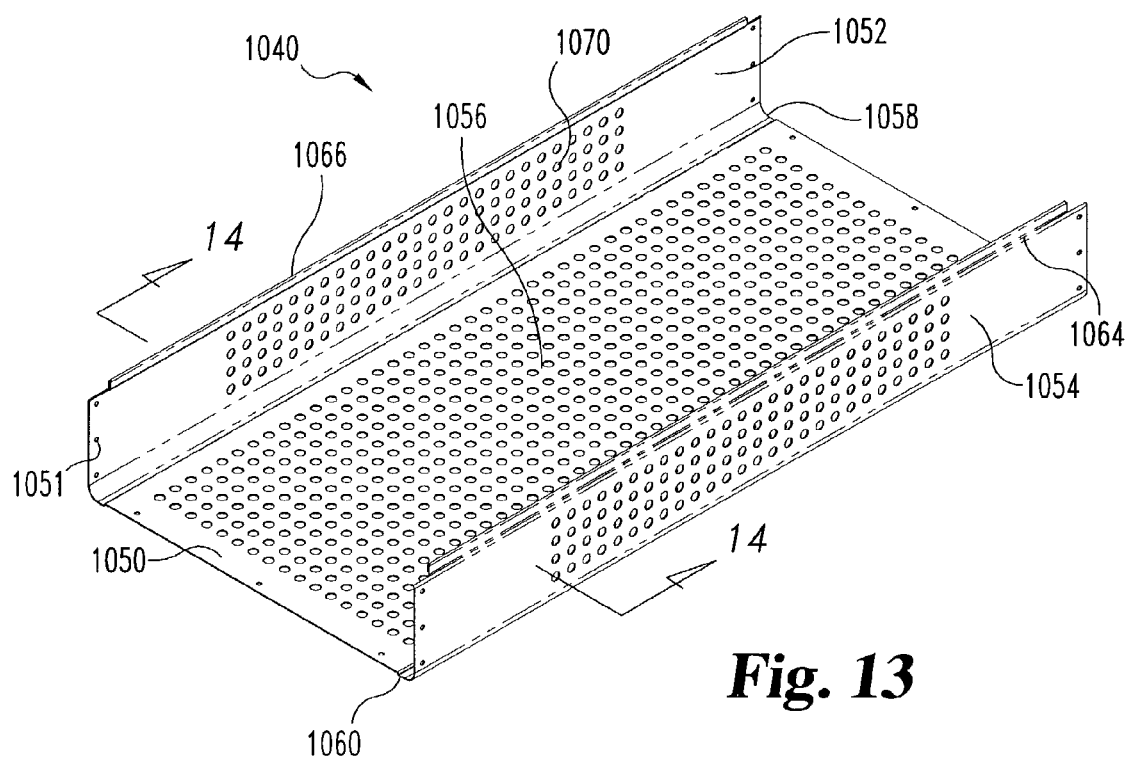
FIG. 13 is a perspective view of a portion of the apparatus of FIG. 11.
Figure 14:
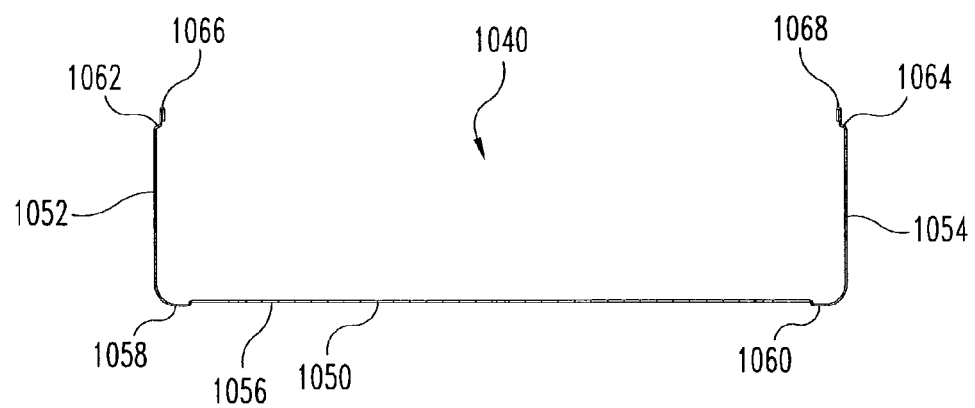
FIG. 14 is a sectional view of the apparatus of FIG. 13 as taken along the line 14—14 of FIG. 13.

FIGS. 13 and 14 depict various features of base midsection 1040. Preferably, base midsection 1040 is fabricated from an integral piece of stainless steel sheet metal, although the present invention contemplates other methods of fabrication, and non-integral base sections as well.

Base midsection 1040 includes a pair of opposing sidewalls 1052 and 1054 which preferably are integral with a bottom 1050. Each lateral edge of base midsection 1040 includes a plurality of fastener holes 1051 for subsequent fastening to respective endwalls. Bottom 1050 includes a central portion for supporting instruments. Central portion 1056 and integral sidewalls 1052 and 1054 further include a plurality of through holes 1070 for the passage of sterilant vapor and liquid during a sterilizing process.

Preferably extending lengthwise along opposing sides of bottom 1050 are channels 1058 and 1060 which provide rigidity to base midsection 1040. Channels 1058 and 1060 laterally interconnect the central portion 1056 to sidewalls 1052 and 1054. Each sidewall projects generally vertically from the corresponding channel. Each sidewall 1052 and 1054 is preferably formed at the free edge to provide mating features and support features for lid 1022.

Referring to FIG. 14, each sidewall 1052 and 1054 includes a formed ridge 1062 and 1064, respectively, and an inwardly and upwardly projecting free edge 1066 and 1068, respectively. Each sidewall 1052 and 1054 is formed such that the corresponding uppermost edge 1066 and 1068 is displaced toward interior 1026 relative to ridges 1062 and 1064, respectively. Preferably, each uppermost edge 1066 ad 1068 includes a rolled-over lip to add stiffness and a non-sharp safety feature to the sidewalls.

Figure 15:
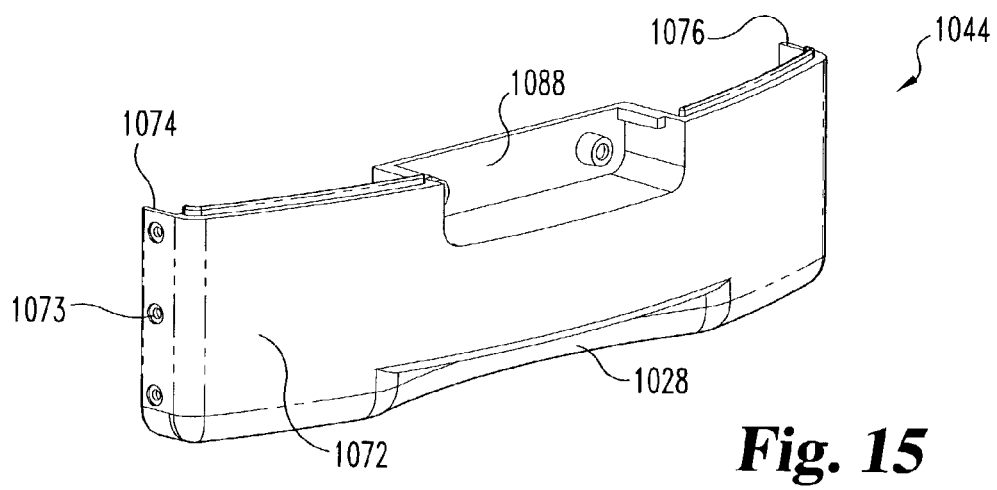
FIG. 15 is a perspective view of a portion of the apparatus of FIG. 11.
Figure 16:
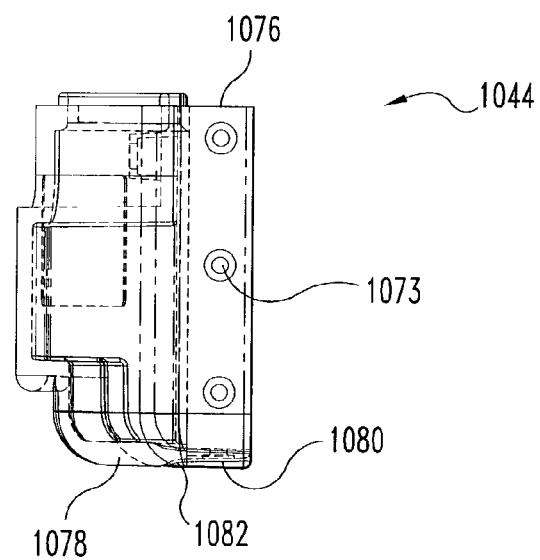
FIG. 16 is an end view of the apparatus of FIG. 15.
Figure 17:
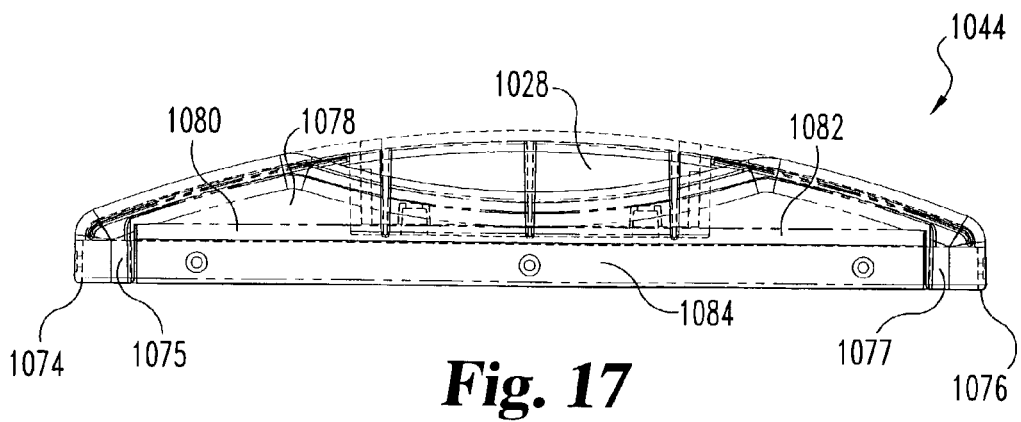
FIG. 17 is a bottom view of the apparatus of FIG. 15.

FIGS. 15, 16, and 17 depict various views of an endwall 1044. Although a single endwall is shown and described, it is understood that a corresponding endwall is preferably attached to the opposite end of container 1020.

Endwall 1044 includes a generally smooth and curving midportion 1072, a pair of laterally-projecting attachment ears 1074 and 1076 located on either end of midportion 1072, and a bottom portion 1078 which spans the bottom area between midportion 1072 and ears 1074 and 1076. Preferably, endwall 1024 is cast or molded from an organic material, although the present invention contemplates any method of fabrication.

As best seen in FIGS. 16 and 17, bottom portion 1078 preferably includes a spacing feature 1080 which provides both stabilization and spacing to a stack of containers 1020, as will be described later. Bottom spacing feature 1080 includes a spanwise planar portion 1084, and a spanwise rounded edge portion 1082 located between planar portion 1084 and the outward surface of midportion 1072. As best seen in FIG. 16, rounded portion 1082 is preferably a concave, or inwardly receding rounded edge. Further, planar portion 1084 is preferably spaced above the bottom most surface of bottom portion 1078.

In one embodiment, endwall 1044 defines a recessed handle 1028 for lifting of container 1020. As best seen in FIG. 17, the finger grip area for handle 1028 is smoothly recessed inwardly from the outermost surface of midportion 1072. In this way, handle 1028 does not present any projections or sharp corners for snagging of clothing on the handle.

Located immediately above handle 1028 is a portion of a pocket 1088 which slidably receives button 1030. As best seen in FIG. 15, pocket 1088 includes a bottom wall, inward wall, and opposing end walls in which button 1030 is placed. Pocket 1088 and button 1030 are adapted and configured such that the outermost surface of button 1030 is generally flush with the outermost surface of midportion 1072. Preferably, pocket 1088 is adjacent to the top of endwall 1044, such that a corresponding endpiece 1036 of lid 1022 provides a top boundary for the pocket.

Referring again briefly to FIG. 1, the relative placement of handle 1028, button 1030 in pocket 1088, and endpiece 1036 provide convenient handling and opening of container 1020. Pocket 1088 and handle 1028 are arranged and configured such that a user's fingers fit within the recess of handle 1028, with fingers or the thumb of the user being positioned to press button 1030 inward. When the user presses button 1030 to release lid 1022, the user's fingers are also located under a surface 1105 of endpiece 1036 (see FIGS. 20–21). Pushing inward on button 1030 simultaneously releases lid 1022 from base 1024, and also places the user's fingers in a position to readily lift lid 1022 upwards. Because the top boundary of pocket 1088 is formed by endpiece 1036, inward movement of the button uncovers portion 1105 of the edge of endpiece 1036.

Placed to either side of spacing feature 1080 are support surfaces 1075 and 1077. Preferably, support surfaces 1075 and 1077 are spaced below spacing feature 1080. Support surfaces 1077 and 1075 support the weight of an assembled container 1020.

Figure 18:
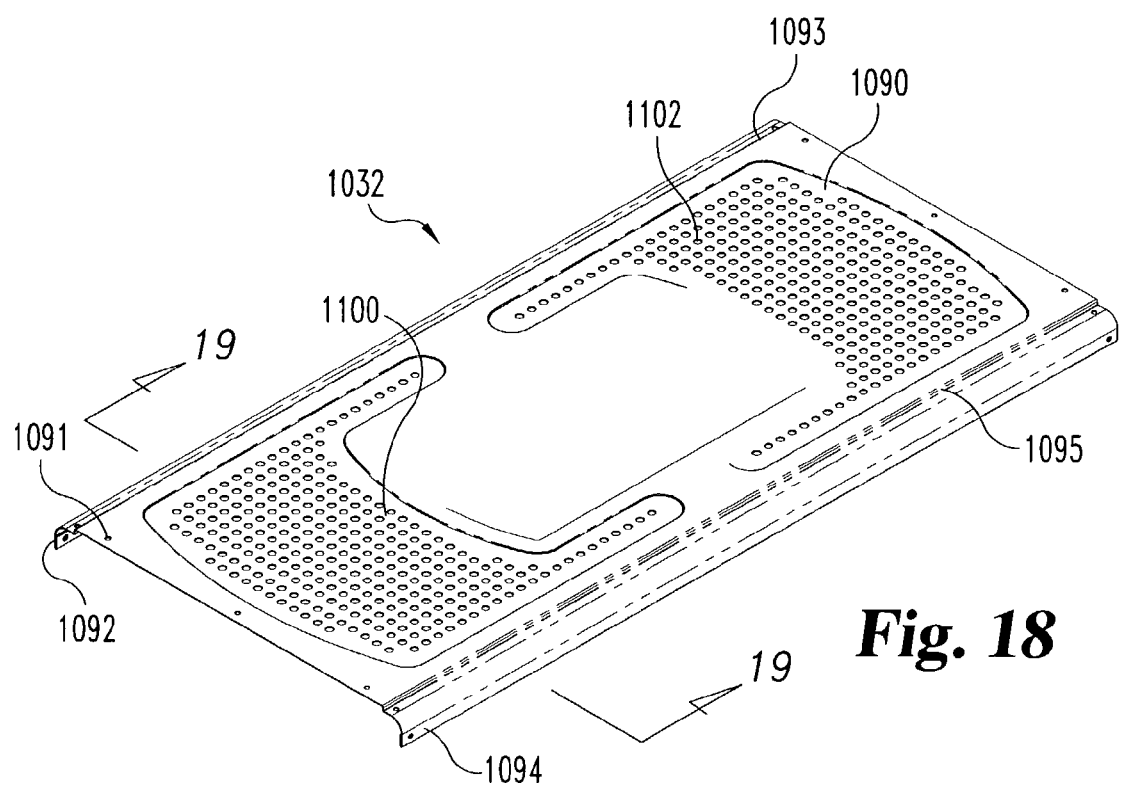
FIG. 18 is a perspective view of a portion of the apparatus of FIG. 11.
Figure 19:
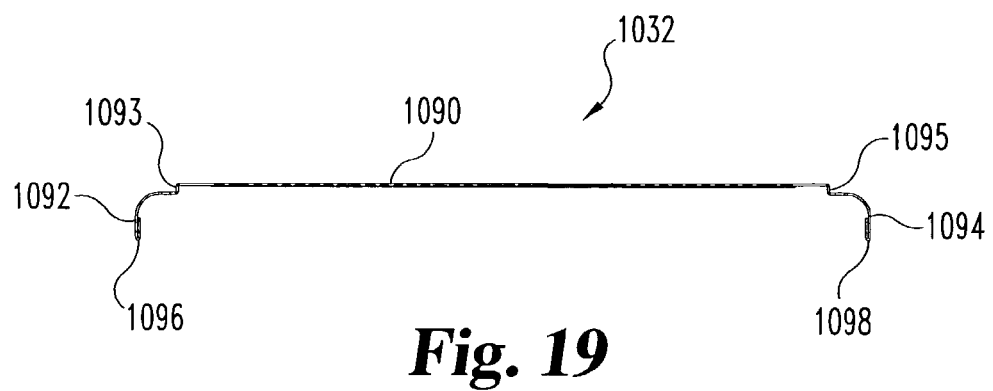
FIG. 19 is a sectional view of the apparatus of FIG. 18 as taken along the line 19—19 of FIG. 18.

FIGS. 18 and 19 show a lid midsection 1032 according to one embodiment of the present invention. Lid midsection 1032 includes a top 1090 and a pair of sides 1092 and 1094 that depend downward from the top. Top 1090 includes a central portion 1100 which preferably includes a plurality of through holes 1102 for passage of sterilant therethrough. Preferably, lid midsection 1032 is formed from a material such as stainless steel sheet metal, although the present invention contemplates any type of fabrication.

Lid midsection 1032 includes a top 1090 having a central portion 1100. A pair of lengthwise ribs 1093 and 1095 are formed along top 1090, and provide stiffness to midsection 1032. Each rib 1093 and 1094 project preferably outwardly and downwardly to sides 1092 and 1094, respectively. Each side 1092 and 1094 include a lowermost edge 1096 and 1098, respectively, which project downwards. Preferably, edges 1096 and 1098 are rolled over for additional stiffness, safety, and for improved fit of lid 1022 on ridges 1062 and 1064, respectively, of base 1024.

Figure 20:
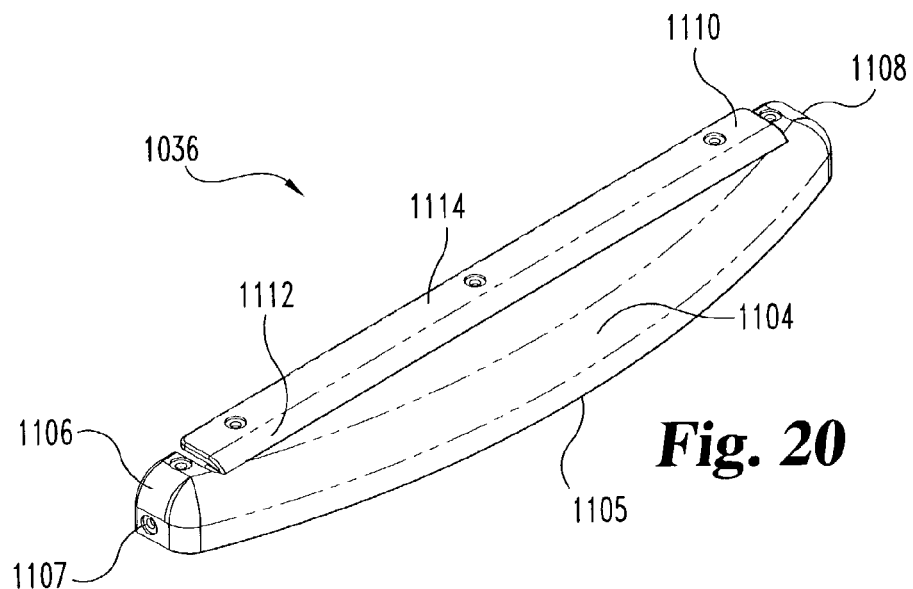
FIG. 20 is a front, top, and left side perspective view of a portion of the apparatus of FIG. 11.
Figure 21:
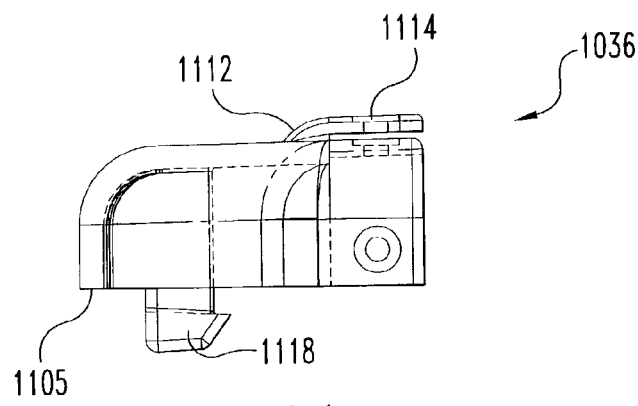
FIG. 21 is a side elevational view of the apparatus of FIG. 20.
Figure 22:
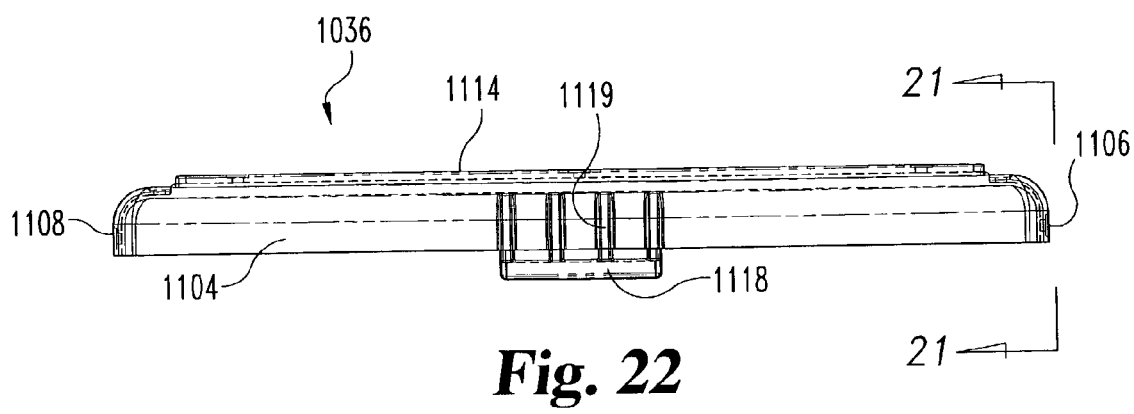
FIG. 22 is a rear elevational view of the apparatus of FIG. 20.

FIGS. 20, 21, and 22 depict various views of an endpiece 1036 according to one embodiment of the present invention. Although a single endpiece will be shown and described, it is understood that lid 1022 preferably includes a similar endpiece located on an opposite end of midsection 1032.

Endpiece 1036 includes a generally smooth and curving midportion 1104 with a pair of ears 1106 and 1108 that project laterally from midportion 1104. Midportion 1104 further includes a downwardly projecting surface 1105 placed centrally that provides an upward boundary of pocket 1088 when a lid 1022 is coupled to a base 1024. Preferably, endpiece 1036 is cast or molded from an organic material, although the present invention contemplates any method of fabrication.

A top portion spanning from ear 1106 to ear 1108 preferably includes a spacing feature 1110 which provides both stabilization to a plurality of stacked containers 1020 and also a predetermined gap between adjacent stacked containers 1020 as will be described later. Spacing feature 1110 includes a convex or outwardly rounded portion 1112 that projects upward from the top of midportion 1104. Rounded portion 1112 transitions smoothly to a planar portion 1114. A plurality of through holes 1107 are provided in endpiece 1036 for fastening of endpiece 1036 to a U-shaped lateral edge of lid midsection 1032.

As best seen in FIGS. 21 and 22, endpiece 1036 includes a hook-shaped latching member 1118 which is centrally located inward of undersurface 1105. Latching member 1118 is supported by a plurality of arms 1119 that project inward and downward from midportion 1104.

Figure 23:
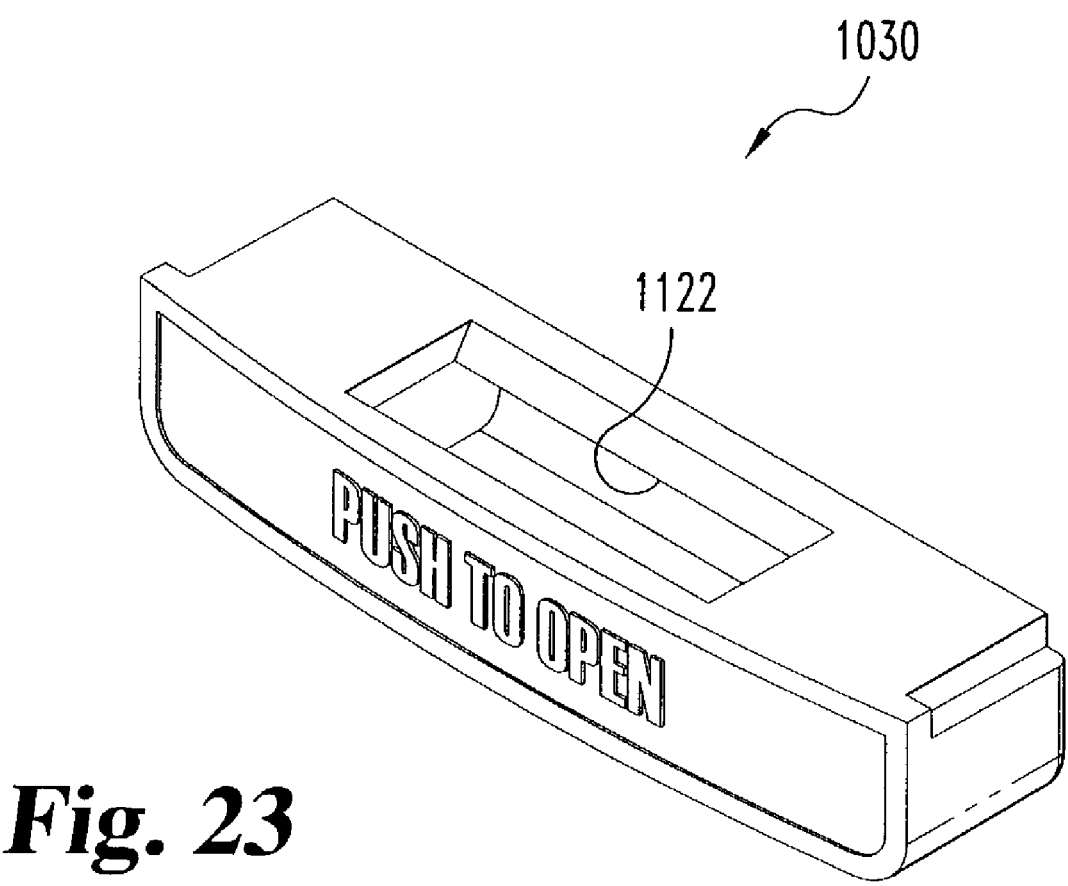
FIG. 23 is a perspective view of a portion of the apparatus of FIG. 11.

FIG. 23 shows a perspective view of a button 1030 according to one embodiment of the present invention. Button 1030 includes a latching member 1122 which is adapted and configured to releaseably couple to the hook of latching member 1118. When button 1030 is biased outwardly to a first, extended, and latched position, latching members 1118 and 1122 couple together such that endpiece 1036, as part of lid 1022, is releaseably coupled to button 1030, which is a part of base 1024.

Figure 24:
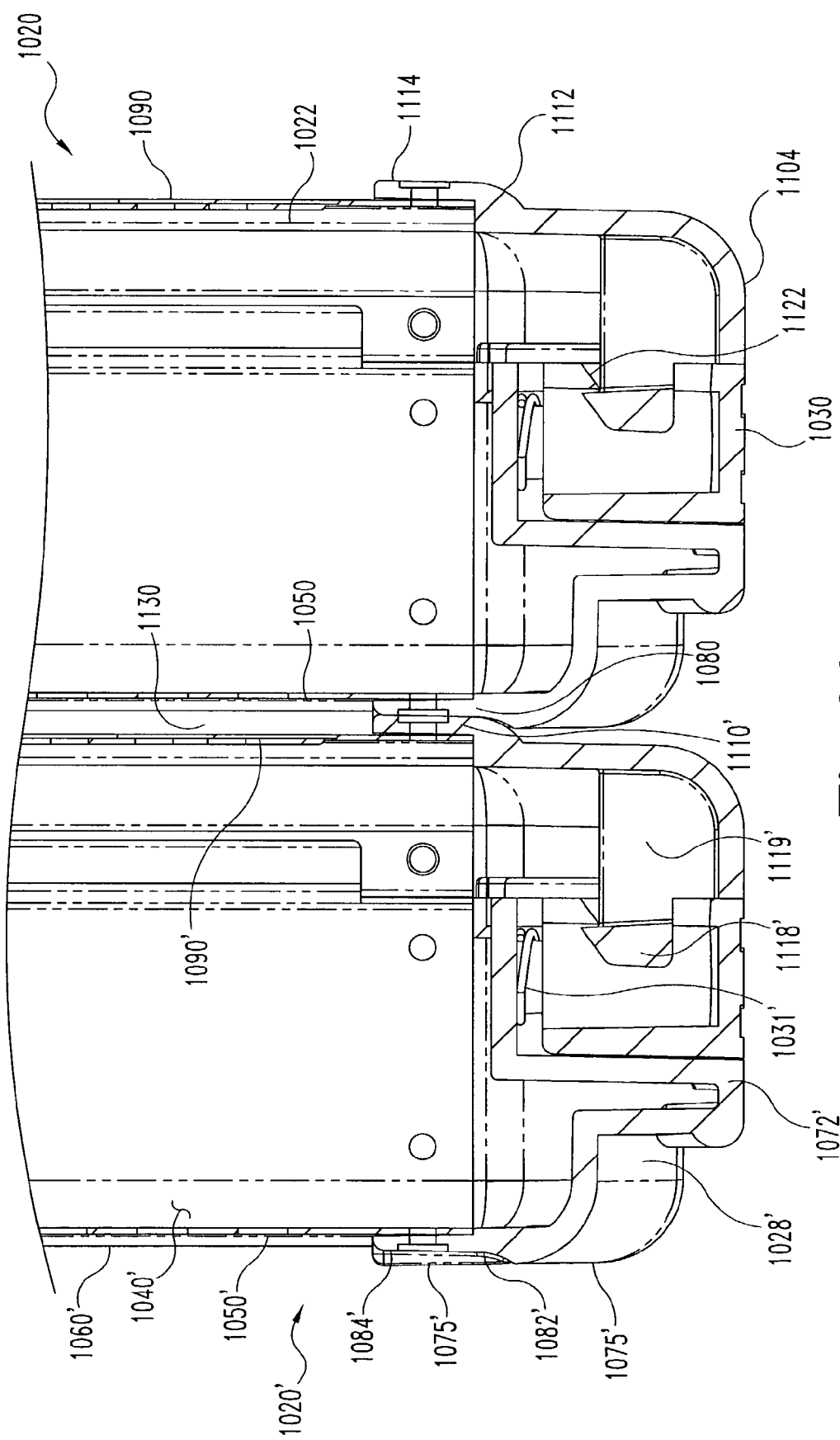
FIG. 24 is a sectional view of a pair of nested containers according to one embodiment of the present invention, the sectional views taken along the line 24—24 of FIG. 11.
Figure 25:
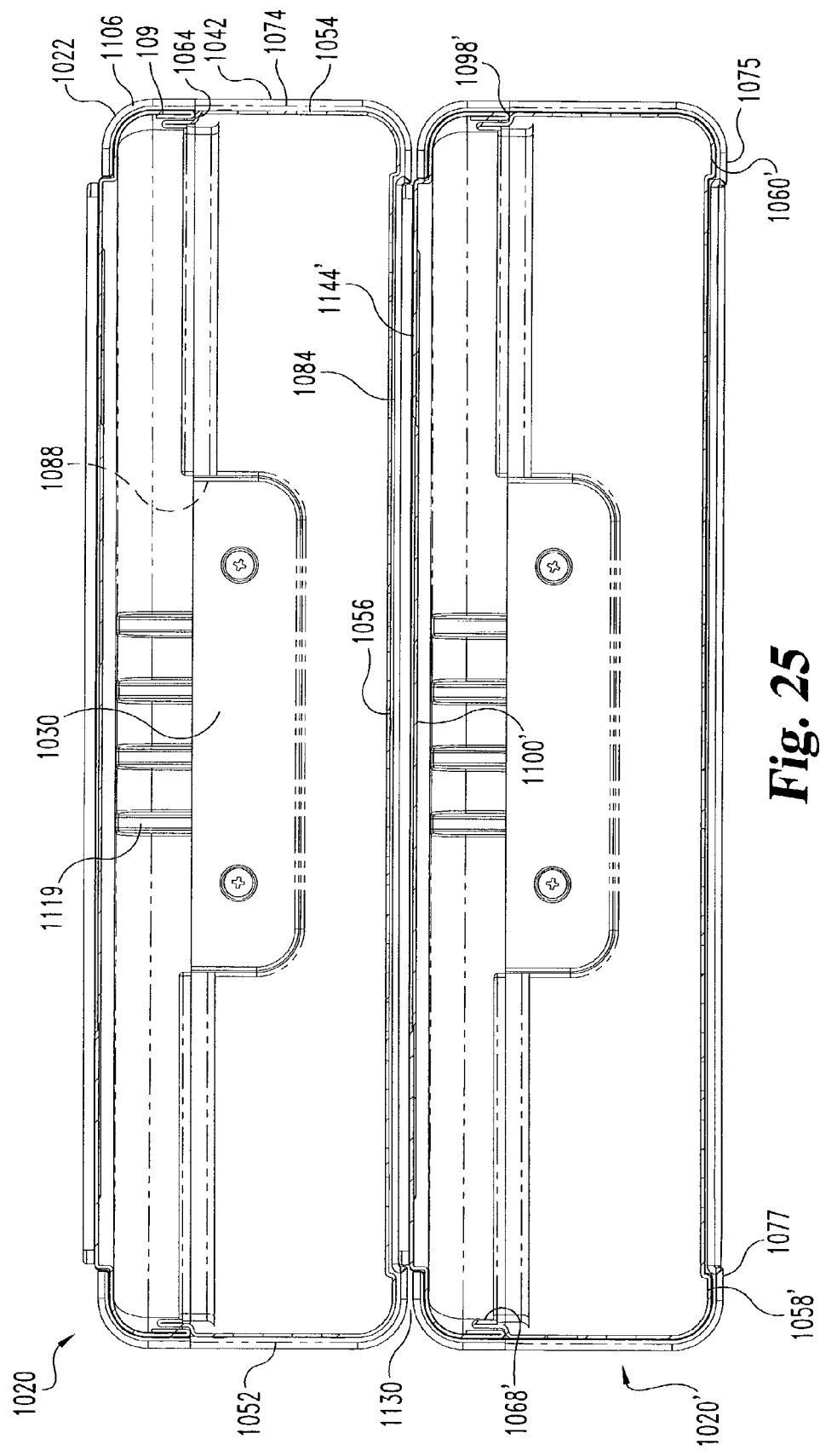
FIG. 25 is a sectional view of a pair of nested containers according to one embodiment of the present invention, the sectional views taken along the line 25—25 of FIG. 11.

FIGS. 24 and 25 present cross-sectional views of a pair of stacked containers. A first container 1020 is stacked on top of a second, identical container 1020'.

In one embodiment of the present invention, top spacing feature 1110 and bottom spacing feature 1080 are preferably shaped complementary to each other, such that convex rounded section 1112 nests within concave rounded feature 1082, as best seen in the middle of FIG. 24. When nested, planar section 1114 of the bottom container supports planar section 1084 of the top container. When sliding a top container 1020 from a position stacked on top of a second, bottom contain 1020', the top container lifts slightly as the rounded portion 1110' of the bottom container forces the rounded portion 1080 of the top container upward. As best seen in FIG. 25, there is a similar, lateral nesting of the lateral edges of a top spacing feature with a bottom spacing feature.

Top spacing feature 1110 and bottom spacing feature 1080 are provided with a thickness or vertical height such that stacking of container 1020 on top of container 1020' results in a gap 1130 formed between bottom 1050 of the top container and top 1090' of the bottom container. As best seen in FIGS. 24 and 25, the relative spacing of spacing features 1080 and 1110 preferably provides a continuous gap 1130 between the sidewalls of base midsection 1040. This gap 1130 preferably extends from one sidewall 1054 to another sidewall 1052 (as best seen in FIG. 25), thus allowing circulation of sterilant vapor from central portions 1056 and 1100' to the outside of the stacked containers. In the embodiment shown in FIG. 24, planar surface 1084' is spaced apart and spaced below the underside surface of bottom 1050'. In addition, the top surface of planar portion 1114 is spaced apart from and spaced above the top surface of top 1090. Further, container support surface 1075 is spaced apart from and spaced below the underside surface of channel 1060'. As best seen in FIG. 24, the weight of a container or stack of containers is supported by contact of surfaces 1075 and 1077 on top of a table or fixture.

Referring to FIG. 25, container 1020 preferably includes an outer surface with smooth, rounded, and flush features. For example, ridge 1064 is adapted and configured such that outer surface of adjacent uppermost edge 1068 is spaced apart from the outer surface of sidewall 1054 by a distance that is about the same distance as the thickness of edge 1098 of lid 1022. With this spacing, as is appreciated in viewing FIG. 25, the outer surface of side 1094 of lid 1022 is flush with the outer surface of sidewall 1054 of vase 1024. Further, the outside surface the ear 1106 of endpiece 1036 is generally smooth and flush with the outer surface of ear 1074 of endwall 1044.

FIG. 26 presents a perspective view of a container 1020" according to another embodiment of the present invention. Container 1020" is identical to container 1020, except that container 1020" is of a shorter overall height, as a result of decreasing the height of sidewall 1054" and midportion 1072". It is further appreciated that the present invention contemplates containers having a variety of different lengths.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A container for sterilization devices comprising:
a tray including a base, a pair of opposing side panels, and a cooperating pair of opposing end walls joined to said side panels for surrounding said base, each end wall having a curved outer surface;
a lid releasably coupled to said tray;
a push-to-release latch button assembled to each end wall and being constructed and arranged to release said lid from said tray, each end wall defining a recessed pocket constructed and arranged to receive said push-to-release latch button, each end wall further defining a recessed handle positioned adjacent said base, wherein each push-to-release latch button having an outermost surface that is generally flush with the curved outer surface of said corresponding end wall, and wherein the push-to-release latch button and the recessed handle of each end wall are constructed and arranged with a size and proximity to permit a plurality of fingers of one hand of a user to fit within the recessed handle while another digit of said same one hand contacts said push-to-release latch button.

* * * * *